Figure 1:
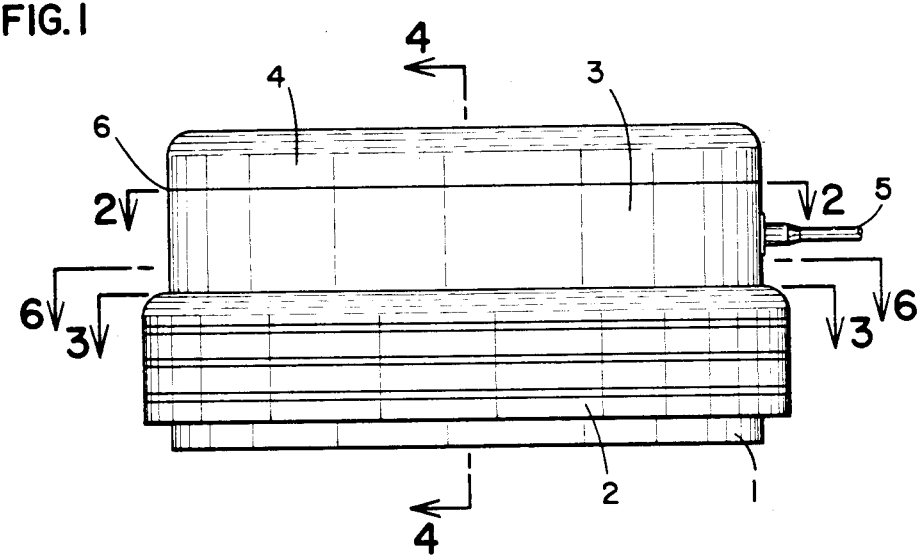

United States Patent [19]

Nielsen

[11] Patent Number: 4,798,535
[45] Date of Patent: Jan. 17, 1989

[54] FOOT REGULATOR, ESPECIALLY FOR DENTAL EQUIPMENT

[76] Inventor: Benny S. Nielsen, Pilegaardsv10 nge 191, DK-2635 Ishoj, Denmark

[21] Appl. No.: 843,111
[22] Filed: Mar. 24, 1986
[51] Int. Cl.⁴ .............................................. A61C 1/02
[52] U.S. Cl. .................................................. 433/101
[58] Field of Search .................. 433/101; 200/153 C, 200/86.5; 251/295; 318/551; 74/527, 512

[56] References Cited

U.S. PATENT DOCUMENTS

| 1,787,262 | 9/1929 | Robertson | 200/7 |
| 1,858,746 | 1/1930 | Miller | 200/7 |
| 2,507,016 | 5/1950 | Hesh | 200/6 A |
| 3,980,848 | 10/1976 | Shulz et al. | 200/153 C X |
| 4,267,804 | 5/1981 | Rypka | 74/527 X |
| 4,527,983 | 7/1985 | Booth | 74/512 X |

FOREIGN PATENT DOCUMENTS

| 2023118 | 5/1970 | Fed. Rep. of Germany. |
| 3302558 | 1/1983 | Fed. Rep. of Germany. |
| 410807 | 12/1974 | Sweden. |

Primary Examiner—Robert P. Swiatek
Assistant Examiner—R. Thomas Price
Attorney, Agent, or Firm—Merchant, Gould, Smith, Edell, Welter & Schmidt

[57] ABSTRACT

A foot regulator which is especially suitable for use in connection with dental treatment equipment consists of a bottom, a control member which is cylindrical and which can be displaced in the horizontal plane and be turned, a housing with a printed circuit supporting a switch, and an upper part. The control member has a recess which in its center position is located immediately under a central hole in the housing, the control pin of the switch extending down into the hole. In the recess there is placed a ball which by the horizontal displacement of the control member will activate the switch, the ball being pressed up into the hole. Turning of the control member is detected by way of optical sensors. By the use of this foot regulator easy and simple operation is obtained in that it can be controlled in the same manner from all sides so that fatiguing working positions for the user can be avoided.

4 Claims, 3 Drawing Sheets

FOOT REGULATOR, ESPECIALLY FOR DENTAL EQUIPMENT

The invention relates to a foot regulator, especially for dental equipment, of substantially cylindrical shape and having a concentric control means which is adapted to be turnable a certain angle on a vertical axis and which is connected with sensing means for sensing the angular turning.

It is advantageous that dental equipment is foot controlled in that the dentist will thus have both hands free for his work with the patient.

There is a pedal provided with a multi-function protruding arm on the market. The arm can be pushed to both sides and thereby control various instruments. If the arm is pressed down, another contact is activated which may for example be used for calling in assistance.

The pedal is furthermore connected to a small computer so that it will automatically control the instrument which the dentist lifts out of the holder.

Moreover, German published specification No. 2,023,118, U.S. Pat. No. 2,200,621 and British patent specification No. 1,492,993 describe control pedals having a rotation symmetrical control means. The means is turnable in the horizontal plane and the position of turning can be sensed for controlling the speed of the rotation of a motor. These pedals can be controlled by the operator from any side.

These known structures have the disadvantage that the speed in the position of rest is zero and will thus before working have to be regulated up to working speed. It is moreover a disadvantage that the same contact function is used for starting and for speed regulation. It thus becomes impossible, for example, to apply different voltages to the two functions. Finally, the known structures use various types of potentio-meters which are subject to wear and which may get dirty with ensuing malfunction.

The object of the invention is therefore to provide a foot regulator where the activation and regulation circuits are electrically separated and where the regulator by being activated, if so desired, will start the motor at a preset speed.

This is achieved when the control means is furthermore displaceable in all directions in the horizontal plane, i.e. in radial directions, and that there are means for sensing such displacement.

If the control means is acted on by a horizontal or radial displacement, this will be registered by the foot regulator which is the signal for start of some instrument. By turning the means the working speed of the instrument can be increased or reduced. The two functions can as a matter of course be electrically separated so that activation may for example take place at a voltage that is different from that of the regulation. The regulator may moreover be made very compact and reliable without many moving parts. The signals from the foot regulator can of course be transmitted to a control unit. The structure moreover ensures that the operator's foot is securely pressed against the means as otherwise the instrument will be disconnected.

If, as disclosed, the control means is spring-loaded towards the position of rest, there is obtained a simple and advantageous design of the regulator.

The centering means may be springs which are horizontally arranged in openings in the control means in that pins extend upwardly from the bottom of the regulator into the openings. There is thus obtained a compact and reliable regulator.

It is advantageous that the means for sensing the displacement are exclusively adapted to register when the control means has left its position of rest. The simplest possible sensing and so an effective regulator is thus obtained.

By a preferred embodiment of the invention the control means can turn either way. There is thereby obtained a further regulating function.

A foot regulator according to the invention can be such that the control means consists of a circular disc which on its upper side is provided with a central recess wherein there is arranged a loose ball, that a housing with a through hole which is coaxial with the recess is arranged on top of the control means, and that a pressure-sensitive switch is arranged by the upper end of the hole.

When the control means is displaced, the ball will be pressed out of the recess and consequently up into the through hole in the plate. Above the hole there is mounted a pressure-sensitive switch such as a microswitch which is provided with a pin or the like extending down into the hole. The ball will therefore activate the switch when the control means is displaced in the horizontal plane.

A further compact structure can—be obtained if the control means is provided with one or more reflecting areas so that its turning can be detected by light-sensitive means. There is moreover obtained a no-touch sensing which is not subject to wear.

If the regulator is designed as disclosed in claim 8, there is obtained effective control of the running of the motor.

Finally, it is advantageous if the foot regulator according to the invention is provided with at least one additional pressure-sensitive switch mounted at the upper side of the foot regulator since such a switch may be used for other working operations such as selection of spray and chip blow.

The invention will be further explained with reference to the drawing wherein

Figure 2:
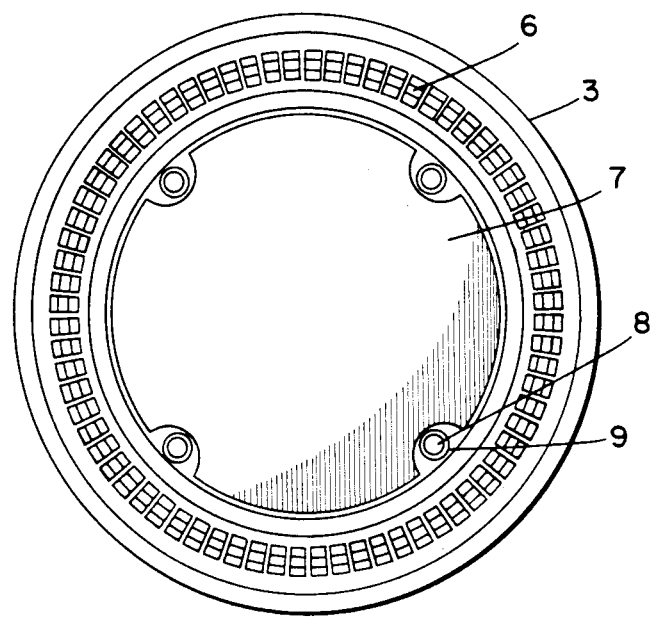
Figure 3:
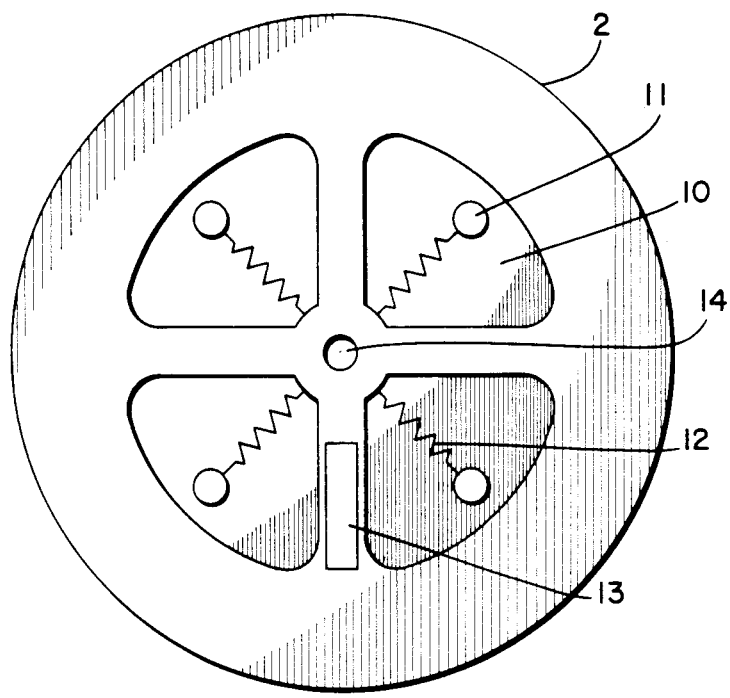
Figure 4:
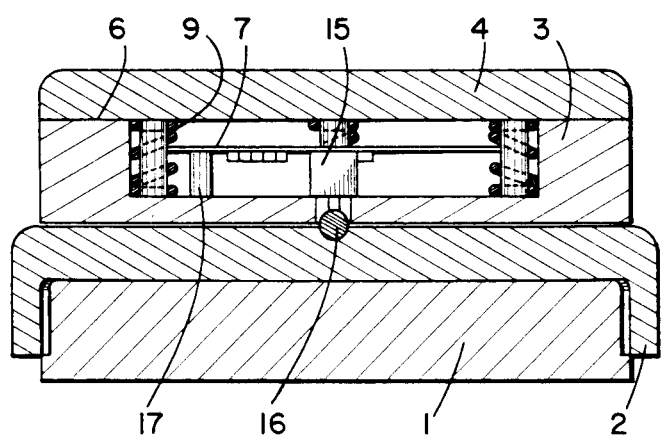
Figure 5:
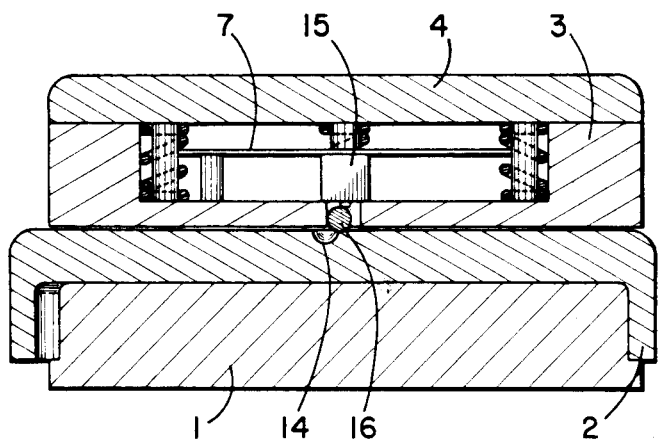
Figure 6:
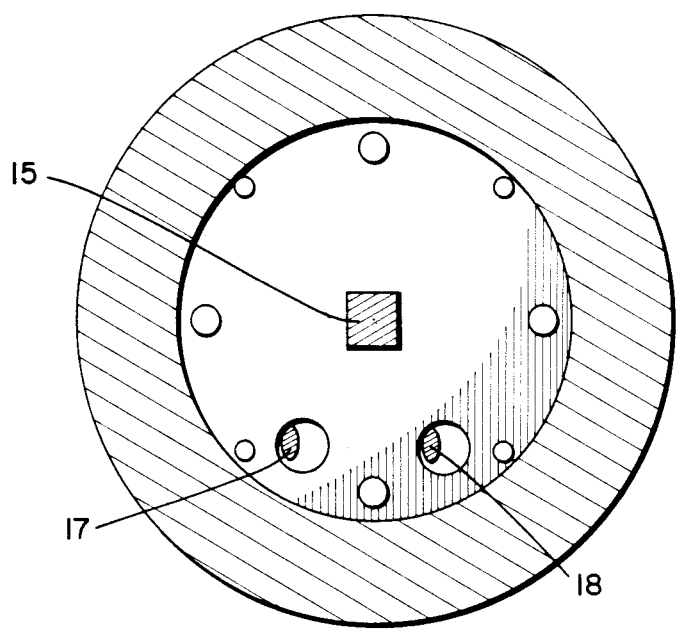

FIG. 1 is an embodiment of a foot regulator according to the invention,

FIG. 2 is a section along line II—II in FIG. 1 seen in the direction of the arrows, FIG. 3 is a section along line III—III and seen in the direction of the arrows, FIG. 4 is a section along line IV—IV seen in the direction of the arrows, FIG. 5 is a section corresponding to FIG. 4 but where the control means is activated, and FIG. 6 is a section along line VI—VI in FIG. 1 seen in the direction of the arrows.

FIG. 1 shows a foot regulator according to the invention. The regulator has a support base 1 whereto by means of springs (see FIG. 3) there is secured a control means 2 being cylindrical. The control means 2 is secured in such a manner that it can be turned in both clockwise and counter-clockwise directions about the vertical axis of the cylinder. Furthermore, it can be displaced a distance in the horizontal plane. On top of the control means 2 there is mounted a housing 3 containing the electronics of the foot regulator. The housing 3 is firmly connected to the base 1 through holes in the control means 2.

On top of the housing 3 there is arranged a pressure-sensitive switch 6. This switch may for example be a circular foil switch. It is activated by the upper part of the foot regulator so that there is thereby obtained yet a contact function.

The regulator may be connected to a control unit, which may for example be a microcomputer, by means of a pilot wire 5.

The regulator is used in the following manner: A displacement in the horizontal plane activates the control means 2 which may now be turned in one direction or the other. If it is turned in one direction, the speed of the connected working instruments is increased, and if turned in the opposite direction, the same speed is reduced.

FIG. 2 shows how the pressure sensitive switch 6 is mounted on top of the housng 3. Inside housing 3 there is arranged a printed circuit 7 which may for example be fastened by screws. The required components are mounted on the circuit board.

To the housing 3 there is moreover secured four upwardly extending pins 8 which are each provided with an internal thread. The upper part 4 may be secured thereto by means of screws. Surrounding the pins there are arranged coil springs 9 so that the upper part will act as a flexible contact.

If the foot regulator is used by a dentist, this control function may for example be used for spray selection and manual chip blow.

FIG. 3 shows a horizontal section of the control means 2. This is provided with four openings 10. From the base 1 four pins 11 extend upwardly, one through each opening. Between the inner section of the control means 2 and the pins 11 there are arranged springs 12 which will centre the control means relative to the base 1 and at the same time allow both horizontal displacement and turning.

The control means 2 is furthermore provided with a reflecting area 13 which is used for detecting turning of the control means. The housing 3 arranged on top of the control means is thus provided with two through holes. In each of these holes there are placed for example a light diode and a phototransistor or a photodiode 17, 18 (FIG. 6). The mode of operation is as follows: When the reflecting area is moved under one of the holes, said area will reflect the light to the light sensor. This signal can then be used for controlling the instrument such that a signal from one hole will increase the speed and a signal from the other hole will reduce the speed.

At the centre of the control means 2 there is a recess 14 the importance of which will be further described in the following.

As will appear from FIGS. 4 and 5, a ball 16 has been placed in this recess 14. The housing 3 is moreover designed with a central through hole. The diameter of this hole is somewhat larger than that of the ball 16. On the printed circuit 7 there is arranged a switch 15 having a control pin extending down into the hole.

As will particularly appear from FIG. 5, the principle is that a horizontal displacement of the control means 2 will force the ball 16 up into the hole where it will activate the switch 15. The position of the switch is moreover shown in FIG. 6 where the photocouplers 17, 18 are also shown.

It is obvious to a person skilled in the art that a foot regulator according to the invention can be designed in many other ways than shown here. The detecting of turning and displacment can also take place in other ways. It is for example possible to imagine a completely optical sensing.

The foot regulator can be manufactured of metal or plastic according to requirements. The electronic components are all commercially available.

The essential feature of the invention is that the foot regulator is controlled in the same way from all sides. It may therefore bring about a substantial relief in the daily work of dentists but will moreover be useable for many other control functions. An example may be the operation of sewing machines.

I claim:

1. A foot regulator of substantially cylindrical shape, for controlling multiple operations upon adjustment; said foot regulator comprising:
(a) concentric control means (2) including a control member mounted for selective rotation about a vertical axis and for selective horizontal displacement, in all radial directions normal to said vertical axis, from a center position;
  (i) said control member having a plurality of radially-spaced openings (10) therein and a plurality of spring members, at least one each of which is mounted in each radiallyspaced opening;
  (ii) said control member having an upper side with a central recess therein;
(b) rotational sensing means for sensing rotational positioning of said control means relative to said vertical axis;
(c) horizontal displacement sensing means constructed and arranged to detect horizontal displacement of said control member from said center position;
  (i) said horizontal displacement sensing means including a ball positioned within said central recess;
  (ii) said foot regulator including a housing having a through-hole therein; said throughhole being aligned coaxially with said control means central recess;
  (iii) said horizontal displacement sensing means including a pressure switch in communication with said ball by means of said through-hole; and,
(d) a plurality of pins mounted in said regulator, at least one each of which extends into one each of said radially-spaced openings in said control member;
  (i) said spring members mounted to extend between said pins and said control member to selectively bias said control member into said center position;
(e) whereby as said control member is horizontally displaced, said ball is displaced at least partially from said recess to activate said pressure switch, said pressure switch being usable to control a first operation; and,
(f) whereby rotational positioning of said control member can be measured by said rotational sensing means for control of a second operation.

2. A foot regulator according to claim 1 wherein said control member is adapted for selective rotation in both counter-clockwise and clockwise manners about said vertical axis.

3. A foot regulator according to claim 1 including an upper surface having a pressure-sensitive switch (6) thereon.

4. A foot regulator of substantially cylindrical shape, for controlling a plurality of operations; said foot regulator comprising:
(a) concentric control means (2) including a control member mounted for selective rotation about a vertical axis, and for selective horizontal displacement, in all radial directions normal to said vertical axis, from a center position; said control member including at least one light reflecting area (13) thereon;

(b) rotational sensing means for sensing rotational positioning of said control member relative to said vertical axis;

(i) said rotational sensing means including light-sensitive means constructed and arranged to register light reflected from said light reflecting area, to sense a rotational positioning of said control means; and, (c) horizontal displacement sensing means constructed and arranged to detect horizontal displacement of said control member from said center position;

(d) whereby horizontal displacement of said control member may be used to control a first operation; and, (e) whereby rotational displacement of said control member may be used to control a second operation.

* * * * *